United States Patent [19]

Lyons

[11] Patent Number: 4,567,045

[45] Date of Patent: Jan. 28, 1986

[54] ISOTONIC GLYCEROL FREE INTRAVENOUS FAT EMULSION

[75] Inventor: Robert T. Lyons, Danville, Calif.

[73] Assignee: Kabivitrum AB, Stockholm, Sweden

[21] Appl. No.: 572,714

[22] Filed: Jan. 20, 1984

[51] Int. Cl.$^4$ .................. A61K 35/78; A61K 31/685; A61K 37/22
[52] U.S. Cl. .................................. 424/195.1; 514/78; 514/561
[58] Field of Search ............ 424/195, 199, 319, 195.1; 514/78, 561

[56] References Cited

U.S. PATENT DOCUMENTS 3,873,720  3/1975  Suzuki et al. .................. 424/312
4,005,190  1/1977  Mader .............................. 424/127

OTHER PUBLICATIONS

Chem. Abst., 74:2500r, J. Schnell, 1971.

*Primary Examiner*—Stanley J. Friedman
*Assistant Examiner*—John W. Rollins, Jr.
*Attorney, Agent, or Firm*—Pollock, Vande Sande & Priddy

[57] ABSTRACT

Sterile, glycerol free lipid emulsion suitable for parenteral administration and including alanine in an amount sufficient to provide pharmaceutically acceptable osmolality.

9 Claims, 4 Drawing Figures

Relative Emulsion Stabilities

Blood Hemolysis Test

A = Distilled water
B = Saline (0.9%)
C = Alalipid (10%)
D = Commercial Fat Emulsion Blood : Soln = 2:1 (v/v)

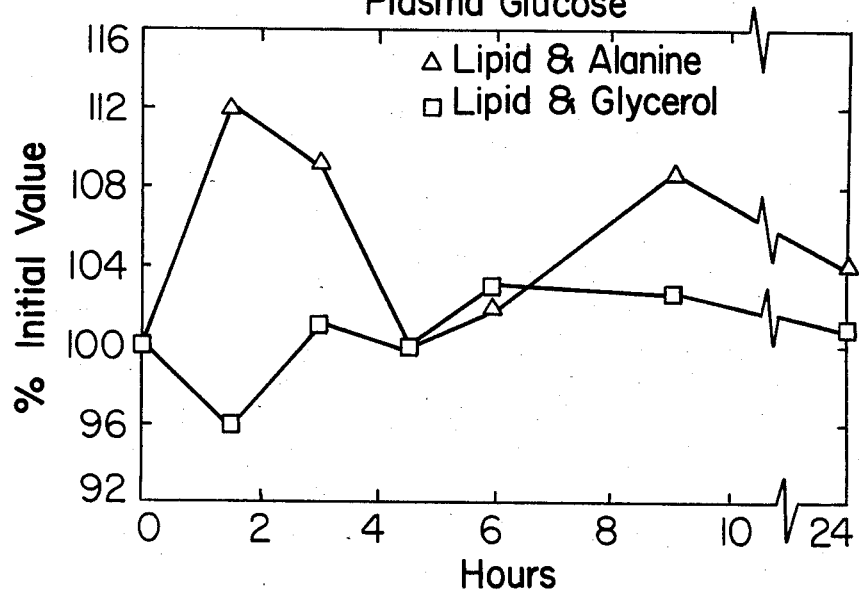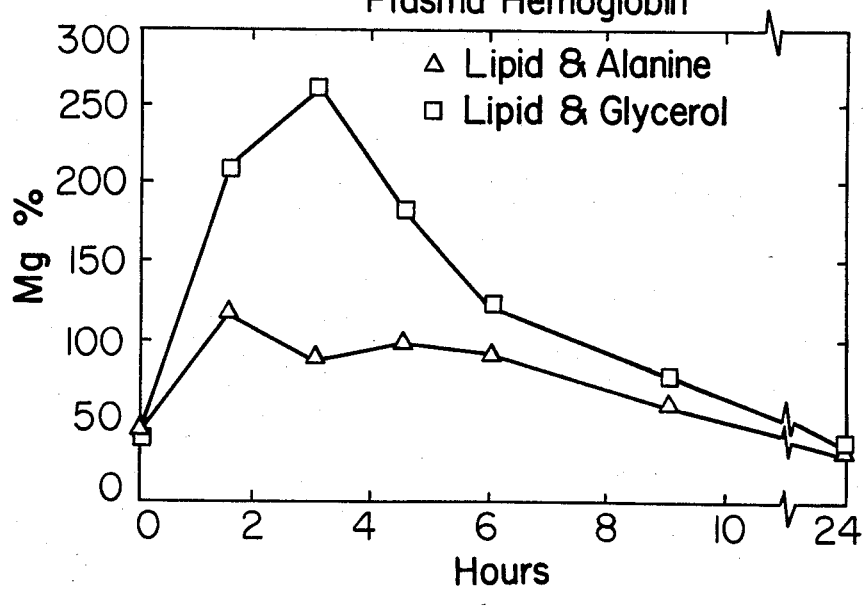

ISOTONIC GLYCEROL FREE INTRAVENOUS FAT EMULSION

BACKGROUND OF THE INVENTION

1. Field

This disclosure is concerned generally with parenteral nutrition and specifically with a novel fat or lipid emulsion suitable for parenteral administration.

2. Prior Art

Lipid emulsions have been widely accepted and used as a means of parenterally administering calories in a highly concentrated form as well as a means of treating or preventing essential fatty acid deficiency during total parenteral nutrition (TPN). It is well known that solutions or emulsions intended for parenteral administration should be physiologically isotonic (i.e. have a pharmaceutically acceptable osmolality) to avoid erythrocyte hemolysis. In the case of aqueous solutions such isotonicity can be assured by the addition of carbohydrates or salts such as sodium chloride. In the case of a fat emulsion, however, salts can be deleterious to emulsion stability. Although the addition of a carbohydrate such as glucose to the aqueous phase does produce a stable, isotonic emulsion, its use can result in undesirable Maillard reactions ("browning") with the free amino groups in phospholipid emulsifiers during thermal sterilization. Because of the above disadvantages, it has been common practice to use glycerol in commercial fat emulsions to assure a pharmaceutically acceptable osmolality without adversely affecting emulsion stability. Such use of glycerol is described, for example, In U.S. Pat. No. 3,109,094 and is used in commercial lipid emulsions (e.g. Intralipid ® I.V. fat emulsion and others).

Although complications are uncommon, there have been numerous reports of acute intravascular hemolysis subsequent to rapid infusion of these glycerol-containing emulsions (Johnstone, A. P., Br. J. Haematol. 50 [2]:376-379 [1982]). In addition, patients on long term TPN receiving intravascular glycerol-containing fat emulsions at proper infusion rates tend to develop low grade anemia which may be due to slight but continuous hemolysis in the peripheral circulation (Marks, L. M., Patel, N., Kurtides, E. S., Am. J. Gastroenterol. 73:490-495 [1980]).

It now appears that all currently marketed fat emulsions are physiologically hypotonic despite the presence of 2.25% w/v glycerol in the formulation. Although a solution of 2.25% glycerol in water has a theoretical (chemical) osmolality of 244 mOsm/l, the effective (biological) osmolality rapidly approaches zero post-infusion due to the high permeability of cell membranes for this solute.

A second problem with glycerol may be the impairment of neutrophil function which has been demonstrated in vitro. This effect may be due to the hypotonicity discussed above and/or to the known ability of glycerol to sequester inorganic phosphate and deplete intracellular ATP (due to rapid formation of glycerol 3-P followed by slow conversion to dihydroxyacetone-P via dehydrogenation) (Burch, H. B. et al., J. Biol. Chem. 257:3676-3679 [1982]). Although the extent to which this occurs in vivo is the subject of current investigation, any impairment of host defenses during TPN would be undesirable.

Finally, glycerol is a poor gluconeogenic substrate in kidney or liver, producing glucose at about ⅓ the rate of lactate or pyruvate (Ross, B. D., Hems, R., and Krebs, H. A., Biochem. J. 102:942-951 [1967]). A new substitute for glycerol in fat emulsions has now been found and details of its use are described below.

SUMMARY OF THE INVENTION

It now appears that a stable, physiologically isotonic fat emulsion can be made by substituting relatively large amounts of L-alanine for glycerol to provide a pharmaceutically acceptable osmolality. This amino acid was chosen because it is neutral at physiological pH, stable to thermal sterilization, relatively low in cost, and, very importantly, it is rapidly removed from circulation by liver and kidney where it is readily transaminated to form pyruvate. See, for example, P. Felig, "The Glucose-Alanine Cycle", pp. 179-207, Metabolism, Vol. 22, No. 2 (Feb.), 1973. This metabolic intermediate may, in turn, either be oxidized for energy via the TCA cycle or be converted to glucose (or liver glycogen) via gluconeogenesis. In addition, it has been reported that L-alanine itself stimulates gluconeogenesis from lactate/pyruvate, probably by reducing recycling of phosphoenolpyruvate back to pyruvate (Ozand, P. T. et al., Biochem J. 170:583-591 [1978] and Nosadini, R. et al., Biochem. J. 190:323-332 [1980]). Thus the presence of L-alanine may even prevent or reduce lactic acidosis which can accompany rapid fat oxidation.

In preferred embodiments, the amount of alanine used to provide a pharmaceutically acceptable osmolality ranges from about 1.0 to 5.0 weight to volume (w/v) %, very preferably about 2.5 w/v %. Preferred osmolality of the resultant emulsion ranges from about 112 mOsm/kg to 560 mOsm/kg of water, very preferably about 280 mOsm/kg. Although a variety of pharmaceutically and nutritionally acceptable lipids may be used, both natural and synthetic, a very preferred lipid is soybean oil emulsified with egg yolk phospholipid and that lipid emulsion was used in the illustrative examples below.

BRIEF DESCRIPTION OF FIGURES

FIG. 3 is a graph comparing plasma glucose levels vs. time following infusion of the emulsion of this disclosure and of a commercial lipid emulsion.

FIG. 4 is a graph comparing plasma hemoglobin levels vs. time following infusion of the emulsion of this disclosure and of a commercial lipid emulsion.

SPECIFIC EMBODIMENTS

Figure 1:
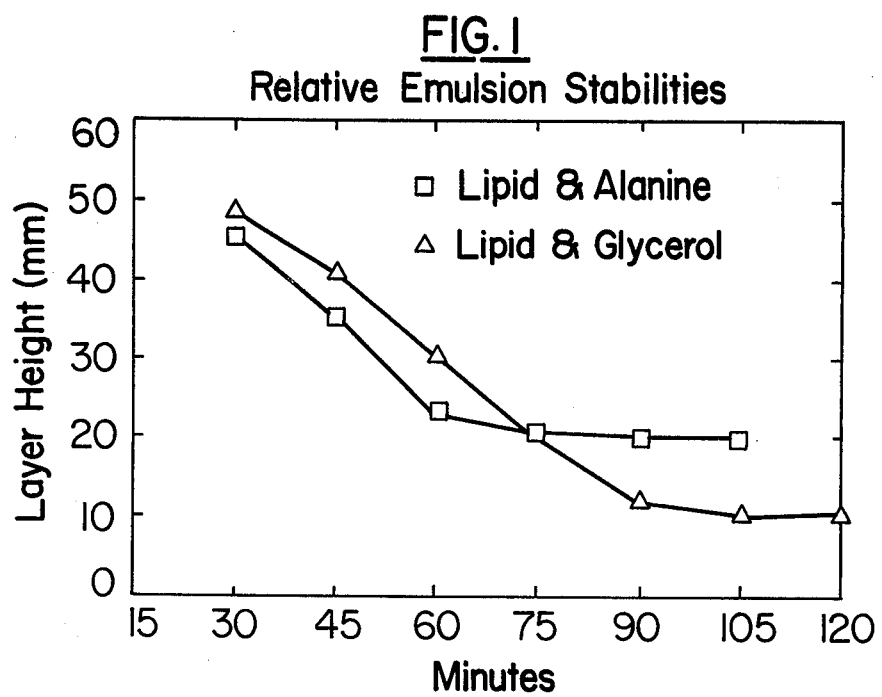
FIG. 1 is a graph comparing relative lipid emulsion stabilities in vitro (accelerated studies) of a commercially available fat emulsion and the glycerol-free emulsion of this invention.

The lipids that may be used in embodying the principles of this disclosure include any nutritionally acceptable lipids that may be given parenterally using either deep (internal) vein or peripheral infusion techniques. The concentration of such lipids may range from about 5% to 50% wt/vol. The invention is especially useful for peripheral infusion where osmolality control is more important due to delayed dispersion of the infused emulsion (cf. deep vein or arterial infusion where dispersion is quicker). The lipids may be natural vegetable fats (e.g. soybean oil, safflower oil, etc.) or synthetic (e.g. structured lipids such as those shown in U.S. Pat. No. 3,450,819 to V. Babayan where both long and medium chain fatty acid residues share the same triglyceride backbone, or physical mixtures of long and medium chain triglycerides). An especially preferred natural fat is soybean oil and a preferred synthetic oil is a synthetic lipid known as CAPTEX 810B available from Stokely-Van Camp Corp. and said to have the following structure:

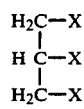

Where X represents long and medium chain fatty acid residues with at least one of each being present and where the long chain fatty acid residue comprises an essential fatty acid and the medium chain fatty acid residue comprises 8 to 12 carbons.

The emulsion may include conventional emulsifiers such as egg yolk phospholipids or other surface active agents and various conventional additives known in the art.

The particle size of the fat of the aqueous emulsion should not exceed 4 microns (preferably, only about 1.5% exceeds 1 micron).

The term pharmaceutically acceptable osmolality means that the emulsion should have a physiologically or biologically acceptable isotonicity, primarily to avoid erythrocyte hemolysis, and this ranges from 112 to 560 mOsm/kg of water. A preferred osmolality for humans is about 280 mOsm/kg. The preferred amount of alanine used ranges from about 1.0 to 5.0 w/v %, preferably about 2.5 w/v %.

It should be noted that this amount of a single amino acid is considerably above any amount used or suggested in the prior art and it is only due to the unusually quick biological uptake and metabolism of alanine that such large amount of a single amino acid is possible in an I.V. infusion without deleterious effects.

Details of the invention are now illustrated below where the combined alanine/lipid emulsion of this invention and the example is referred to as "alalipid" unless otherwise indicated.

EXAMPLE

Preparation of Fat Emulsion

An alalipid sample was made having the following composition: 10% soybean oil, 1.2% purified egg yolk phospholipid, 2.5% (w/v) L-alanine and distilled water to 100% volume. Alanine (Ajinomoto Chemicals) was dissolved in the aqueous phase prior to emulsification. Intralipid ® 10% fat emulsion, used here as the control emulsion, was from a commercial lot and contained 2.25% glycerol (as is conventional) rather than the L-alanine.

Acute Infusion Study in Dogs

Groups of three fasted beagle dogs were placed in Pavlov slings and given an I.V. infusion of either Intralipid 10% (wt. %) or alalipid 10% (wt. %) at 1 g fat/kg/hr for 3 hrs. via a peripheral catheter (leg vein). Upon completion of the infusion, animals were placed in individual cages for the remainder of the study period. Blood samples were collected by venipuncture at 0, 1.5, 3, 4.5, 6, and 9 hrs. post-initiation of infusion and were anti-coagulated with citrate.

Biological Tonicity

Fresh whole rat blood was anti-coagulated with citrate and then mixed with the test solution or emulsion (2:1 v/v) in small tubes, inverted, and then centrifuged 10' at 2800 rpm to sediment intact erythrocytes. The extent of hemolysis was estimated from the color of the resulting supernatant, scored relative to saline (+0) and distilled water (+4).

7-Day Infusion Study in Rats

Male Sprague-Dawley rats (Charles River) weighing 240–280 gms were selected at random and were infused (5 per group) via a central venous catheter with either Intralipid 10% or Alalipid 10% for 20 hrs. per day at a dose of 9 gms fat (90 ml emulsion) per kg body weight for 3 or 7 consecutive days. Control rats received a saline infusion via the same route.

A supplemental, fat deficient, oral diet was offered to both groups, with the Intralipid rats pair-fed to the amounts consumed by the Alalipid group. The composition of the oral diet was as follows:

l-methionine: 3.0
Casein: 275.0
Sucrose: 406.0
Corn Starch: 203.0
Corn Oil: 10.0
Choline Chloride: 3.0
Vitamin Mixture: AIN-76 TM : 15.0
Salt Mixture: Modified Bernhart-Tomarelli: 75.0
Cellulose: Alphacel ®: 10.0

In addition, tap water was available to all rats ad libitum.

Characterization of the Fat Emulsion

The substitution of L-alanine for glycerol in a 10% soybean oil emulsion results in a product acceptable by commercially established release specifications. Particle size is well within limits, with only 1.5% exceeding 1 micron and with no visible floating oil droplets. Stability, as measured by a standardized centrifugal assay, is comparable to Intralipid ® product (FIG. 1). The results of an accelerated ageing show that after 3 months at 40° C., there is a 0.96 unit pH drop for Intralipid, but only a 0.11 unit drop for the alalipid, probably due to the zwitterion character of alanine which serves as a buffer. For both emulsions free fatty acid levels remain within specifications, less than 5 mEq/l. Buffering agents such as alanine may be expected to prolong shelf life by retarding the fall in pH which both accompanies and accelerates spontaneous lipolysis.

Figure 2:
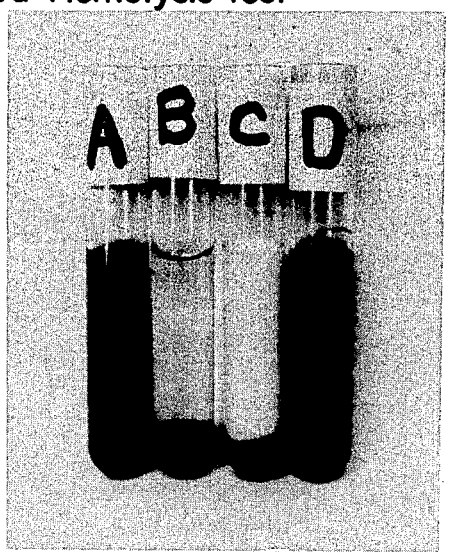
FIG. 2 is a photograph of four test tubes comparing the relative amounts of red blood cell hemolysis in distilled water (A), normal (0.9%) saline (B), the emulsion of this invention (C), and a commercially available lipid emulsion (D).

The hemolytic action of current commercial fat emulsions (10% or 20%) can be readily demonstrated in vitro by mixing anti-coagulated whole blood with the test emulsion as described under Methods. As shown in FIG. 2, the commercial product behaves essentially like distilled water and causes nearly total hemolysis under these conditions, while alalipid is equivalent to physiological (0.9%) saline, with no visible hemolysis. Since the resistance of human erythrocytes to hemolysis is reported to change in certain disease states, it would appear especially desirable to improve the "safety margin" of I.V. fat emulsions by increasing the effective osmolality.

Rat blood was used in order to increase the sensitivity of this "biotonicity" assay; dog or human erythrocytes are reported to be more resistant to hypotonic solutions. It should be emphasized that while these test conditions are non-physiological, we are able to differentiate between chemical and biological tonicity. Obviously, this hemolysis test could be made more quantitative and more sensitive by assaying hemoglobin (or elemental iron or phosphorus) in the supernatant fraction.

Acute Infusion Study in Dogs

This study was performed as described above. The dogs tolerated the acute infusion of alalipid (1 gm fat/kg/hr for 3 hrs.) very well with no untoward clinical reactions.

Plasma aminograms revealed only a slight decrease in most amino acids during infusion, attributed to hemodilution. Alanine, however, rose rapidly to 8-fold baseline levels, peaked at 1.5 hrs, and then returned to pre-infusion values by 6 hrs.

As expected, there were increases in plasma glucose (FIG. 3) and immuno-reactive insulin (not shown) during the alalipid infusion in contrast to much smaller changes with the Intralipid ® product. These results are consistent with more rapid gluconeogenesis from alanine than from glycerol in Intralipid. The reason for the apparent "biphasic" glucose response from alalipid is not clear, but could be related to enhanced glycogenolysis following glucagon secretion in response to alanine infusion.

Two potentially adverse observations were made during this study. Total plasma urea nitrogen rose 50% to a peak at 3 hrs and then gradually declined to basal levels by 24 hrs. Dogs receiving the Intralipid product showed no such changes during this time course. Furthermore, over one third of the infused alanine was excreted by 9 hours.

Given the acute nature of this study in which 30 ml of fat emulsion containing 750 mg of alanine per kg body weight was infused within 3 hrs, elevations in plasma urea nitrogen and significant renal clearance of alanine are not surprising. Of equal importance is the apparent low toxicity and rapid clearance of plasma alanine and the minimal perturbations observed in levels of other amino acids.

An important theoretical benefit of alalipid was also confirmed. As shown in FIG. 4, Intralipid infusion resulted in marked intravascular hemolysis as measured by plasma hemoglobin, with much smaller effects from alalipid. These results in vivo confirm the in vitro (visual) comparison regarding hemolysis that is evident from the photos of FIG. 2.

3 and 7-Day Infusion Study in Rats

A daily I.V. infusion of 10% fat emulsion in male rats was performed for the purpose of determining the metabolic fate and tolerance of alalipid (AL) compared to an Intralipid ® (IL) control. The experimental design has been described above.

Mean daily changes in body weight for rats in each group were measured and these data establish that rats assigned to each group were growing at statistically indistinguishable rates prior to initiation of infusion. There were also no significant differences between mean growth rates on IL vs. AL after either 3 or 7 days (paired t-test).

Mean daily food consumption was measured and these data indicate that pair-feeding has kept total energy intake (infused+oral calories) essentially the same for both test groups. Pair-feeding was necessary since alalipid rats were expected to consume less supplemental (oral) diet than the Intralipid ® product group.

There were some small but significant differences between treatment groups in plasma levels of certain amino acids. In the case of lysine, both groups were similar but both were elevated over pre-infusion (saline) controls. Elevated glutamine (and asparagine) in the alalipid group is an expected result of transamination of alanine to pyruvate. Deamination of glutamine during sample handling and storage could explain elevated glutamate and ammonia (especially in the 7-day alalipid group). The metabolic significance of other changes which include elevated leucine and tyrosine and reduced serine and glycine is not clear at this time, although these differences apparently are not sufficient to inhibit growth in body weight. Interestingly, alanine itself was not elevated in the alalipid group.

Blood chemistry results were studied. Of particular concern was the apparent elevation in serum cholesterol in the alalipid rats. This may be a consequence of some difference in the chemical composition of emulsion egg yolk phospholipid, or emulsion particle size or, less likely, may be an effect of alanine itself or reflect some hormonal changes induced by alanine. This elevation in serum cholesterol will require further investigation. Other blood chemistries including BUN, triglycerides, and glucose levels showed no important differences from controls.

When alalipid was administered at 90 ml/kg body weight (thus delivering 2.25 g alanine/kg over 20 hrs) there was almost complete metabolism of alanine with no statistically significant changes in daily urinary excretion of either total nitrogen or alanine, when compared to IL control. The discrepancy in these excretion results with rats when compared to the previous 3 hr dog infusion study may be due to (a) species differences, or (b) induction of glutamic-alanine aminotransferase during chronic infusion, and/or (c) lower rates of administration of alanine (dog=250 mg/kg/hr, rat=112 mg/kg/hr).

The addition of L-alanine in place of glycerol as a means of producing an isotonic I.V. fat emulsion appears to be a better means of providing pharmaceutically acceptable osmolality in a fat emulsion, although further metabolic and safety studies are required. Advantages of using alanine may be summarized as follows:

(1) Buffering an emulsion via alanine may prolong shelf life by reducing the rate of pH drop associated with release of free fatty acids.

(2) A biologically isotonic emulsion may increase the margin of safety with respect to intravascular hemolysis, especially for peripheral infusions, and may reduce the tendency towards low-grade anemia frequently associated with long-term TPN.

(3) Alalipid is a stable emulsion containing a highly efficient gluconeogenic substrate, thus providing a carbohydrate energy supplement without undesirable Maillard reaction products.

(4) Alanine (more than any other amino acid) is rapidly cleared from circulation without causing growth-inhibiting amino acid imbalances and without increasing renal excretion loads.

(5) Omission of glycerol may alleviate putative impairments in neutrophil function following infusions with I.V. fat emulsions.

Given the above disclosure, it is thought variations will occur to those skilled in the art. Accordingly, it is intended that the above examples should be construed as illustrative only and that the scope of the invention disclosed should be limited only by the following claims.

I claim:

1. A lipid emulsion suitable for parenteral administration, the emulsion being substantially free of glycerol and including L-alanine in an amount sufficient to provide a pharmaceutically acceptable osmolality, and wherein the amount of alanine ranges from about 1.0 to about 5.0 w/v %.

2. The emulsion of claim 1 wherein the osmolality of the emulsion ranges from about 112 to about 560 mOsm/kg.

3. The emulsion of claim 2 wherein the osmolality ranges from about 168 mOsm/kg to 393 mOsm/kg.

4. The emulsion of claim 1 wherein the lipid is selected from the group consisting of natural and synthetic lipids.

5. The emulsion of claim 4 wherein the lipid is a nutritionally acceptable natural lipid.

6. The emulsion of claim 5 wherein the lipid is selected from the group consisting of soybean, safflower, and sunflower oils.

7. The emulsion of claim 4 wherein the lipid is a nutritionally acceptable synthetic oil which, on hydrolysis, yields both long and medium chain fatty acid.

8. The emulsion of claim 1 wherein the lipid is soybean oil and comprises about 2.5% w/v % L-alanine, the emulsion having an osmolality of about 280 mOsm/kg and being suitable for peripheral administration.

9. The emulsion of claim 1 wherein the concentration of lipid ranges from about 5 to about 50 wt/v %.

* * * * *